(12) United States Patent
Eckhardt et al.

(10) Patent No.: US 8,173,490 B2
(45) Date of Patent: May 8, 2012

(54) FABRICATION OF ELECTRONIC DEVICES INCLUDING FLEXIBLE ELECTRICAL CIRCUITS

(76) Inventors: Helmut Eckhardt, Cary, NC (US); Stefan Ufer, Raleigh, NC (US)

(*) Notice: Subject to any disclaimer, the term of this patent is extended or adjusted under 35 U.S.C. 154(b) by 0 days.

(21) Appl. No.: 13/008,338

(22) Filed: Jan. 18, 2011

(65) Prior Publication Data

US 2011/0117703 A1 May 19, 2011

Related U.S. Application Data

(62) Division of application No. 12/333,448, filed on Dec. 12, 2008, now Pat. No. 7,898,074.

(51) Int. Cl.
*H01L 21/768* (2006.01)

(52) U.S. Cl. .................. 438/118; 257/E21.576

(58) Field of Classification Search .......... 257/690–693, 257/E23.055, E23.065, E23.177; 438/118
See application file for complete search history.

(56) References Cited

U.S. PATENT DOCUMENTS

| | | | |
|---|---|---|---|
| 5,109,844 A | 5/1992 | de Juan, Jr. et al. | 128/419 |
| 5,597,381 A | 1/1997 | Rizzo, III | 623/4 |
| 5,935,155 A | 8/1999 | Humayun et al. | 607/54 |
| 6,071,597 A | 6/2000 | Yang et al. | 428/209 |
| 6,221,769 B1 | 4/2001 | Dhong et al. | 438/667 |
| 6,368,349 B1 | 4/2002 | Wyatt et al. | 623/6.63 |
| 7,142,909 B2 | 11/2006 | Greenberg et al. | 607/2 |
| 7,146,221 B2 | 12/2006 | Krulevitch et al. | 607/116 |
| 7,294,914 B2 | 11/2007 | Liebeskind | 257/678 |
| 7,326,649 B2 | 2/2008 | Rodger et al. | 438/669 |
| 7,417,310 B2 * | 8/2008 | Szewerenko et al. | 257/696 |
| 2002/0182778 A1 | 12/2002 | Wang et al. | 438/119 |
| 2003/0057567 A1 | 3/2003 | Hedler et al. | 257/778 |
| 2005/0017345 A1 | 1/2005 | Sathe | 257/700 |
| 2005/0236361 A1 | 10/2005 | Ufer et al. | 216/41 |
| 2005/0263909 A1 | 12/2005 | Fukuta et al. | 257/784 |
| 2006/0225274 A1 | 10/2006 | Greenberg et al. | 29/846 |
| 2007/0067000 A1 | 3/2007 | Strother et al. | 607/36 |
| 2007/0158100 A1 | 7/2007 | Greenberg et al. | 174/254 |
| 2007/0191909 A1 | 8/2007 | Ameri et al. | 607/54 |
| 2008/0046021 A1 | 2/2008 | Greenberg et al. | 607/36 |
| 2008/0046080 A1 | 2/2008 | Vanden Bulcke et al. | 623/10 |
| 2008/0051848 A1 * | 2/2008 | Greenberg et al. | 607/36 |
| 2008/0058895 A1 | 3/2008 | Ok et al. | 607/54 |
| 2008/0077194 A1 | 3/2008 | Greenberg et al. | 607/54 |
| 2008/0077195 A1 | 3/2008 | Greenberg et al. | 607/54 |
| 2008/0086173 A1 | 4/2008 | Ok et al. | 607/2 |
| 2008/0086206 A1 | 4/2008 | Nasiatka et al. | 623/6.14 |

OTHER PUBLICATIONS

Liu et al., "A Neuro-Stimuilus Chip with Telemetry Unit for Retinal Prosthetic Device", *IEEE Journal of Solid-State Circuits*, vol. 35, No. 10, pp. 1487-1497 (Oct. 2000).

(Continued)

*Primary Examiner* — Zandra Smith
*Assistant Examiner* — Paul Patton
(74) *Attorney, Agent, or Firm* — David P. Gloekler; The Eclipse Group, LLP.

(57) ABSTRACT

A packaged electronic device includes a die, a flexible circuit structure, and a barrier film disposed on the die. The die includes die circuitry and electrical contacts. The flexible circuit structure is bonded directly to the die, and includes electrical conductors encapsulated by structural layers. Each electrical conductor contacts a respective electrical contact. The electronic device is encapsulated by the barrier film and one or more of the structural layers.

21 Claims, 10 Drawing Sheets

OTHER PUBLICATIONS

Stieglitz et al., Micromachined, Polyimide-Based Devices for Flexible Neural Interfaces, *Biomedical Microdevices*, vol. 2, No. 4, pp. 283-294 (2000).

Quinones et al., Flip Chip and Chip Scale Packaging Technologies: A Historical Perspective and Future Challenges, *Semicon China 2000 Technical Symposium*, pp. A-1 to A-10 (2000).

Meyer et al., High Density Interconnects and Flexible Hybrid Assemblies for Active Biomedical Implants, *IEEE Transactions on Advanced Packaging*, vol. 24, No. 3, pp. 366-374 (Aug. 2001).

Margalit et al., Retinal Prosthesis for the Blind, *Survey of Ophthalmology*, vol. 47, No. 4, pp. 335-356 (Jul.-Aug. 2002).

Fjelstad et al., Chip-Scale Packaging for Modern Electronics, *Electrochemical Publications*, 3 pg summary with full Contents List and author's Preface—25 pgs (2005).

Ghovanloo et al., A Modular 32-Site Wireless Neural Stimulation Microsystem, *IEEE Journal of Solid-State Circuits*, vol. 39, No. 12, pp. 2457-2466 (Dec. 2004).

Solzbacher, Chronic Mecroelectrode Recording Array, Contract NINDS-NIH N01-NS-4-2364, 15 pgs (2004-2008).

International Search Report and Written Opinion From Corresponding PCT Application No. PCT/US2009/066042, Jul. 1, 2010 (9 pgs).

* cited by examiner

FABRICATION OF ELECTRONIC DEVICES INCLUDING FLEXIBLE ELECTRICAL CIRCUITS

RELATED APPLICATIONS

This application claims the benefit of U.S. patent application Ser. No. 12/333,448, filed Dec. 12, 2008, titled "ELECTRONIC DEVICES INCLUDING FLEXIBLE ELECTRICAL CIRCUITS AND RELATED METHODS;" the content of which is incorporated by reference herein in its entirety.

BACKGROUND OF THE INVENTION

1. Field of the Invention

This invention relates generally to electronic devices and the packaging thereof, including but not limited to hermetic and/or biocompatible packaging or sealing that renders such electronic devices environmentally isolated and/or implantable in vivo or in vitro. More particularly, the invention relates to electronic devices that include flexible circuit structures integrally bonded to and embedded with die structures, and assemblies or systems that include or cooperate with such electronic devices.

2. Related Art

An ongoing need exists for advances in electronic device miniaturization, packaging of integrated circuits and associated microfabrication technologies to enable new and improved implementations of electronic devices. Up to the present time, flip-chip technology as applied to bare dies has been considered to be the assembly process achieving the highest packing density, smallest footprint and lowest profile. For a detailed discussion of trends and challenges in state-of-the-art chip packaging (chip scale packaging, CSP and flip-chip), see Fjelstad et al., *Chip scale packaging for modern electronics*, Electrochemical Publications Ltd. (2002); Quinones et al., *Flip-chip and chip scale packaging technologies: A historical perspective and future challenge*, SEMICON China 2000 Technical Symposium: A1-A9 (2000). Briefly, in the flip-chip process the die is assembled face down onto the substrate (rigid board or flexible) with an array of solder bumps making electrical connection to the substrate. Reliability of the interconnects in flip-chip has been a great concern in the industry. This is particularly true for bonding to organic substrates because of the difference in thermal expansion coefficients between the chip and the substrate. Usually epoxies are used as underfill materials to make structures mechanically stronger and to improve reliability.

The need for further advances extends to environmentally isolated and/or biocompatible devices. Examples of biocompatible devices include implantable neural prostheses designed to interface with the nervous system to restore lost functions such as movement, hearing or vision. Other examples of neurostimulation devices include, without limitation, devices envisioned for spinal cord stimulation, deep brain and vagus nerve stimulation, sacral nerve stimulation, and gastric electrical stimulation. The requirements for such advanced implants are very different from implant devices found in the market today. The best known and commercially most successful implant is the cardiac pacemaker developed more than 30 years ago. Like the pacemaker, many of the FDA-approved implant devices use rigid packaging like titanium or ceramic casings for hermetic sealing and are equipped with mostly single or low-density microelectrodes for sensing and delivery of electrical stimulation. The electrodes and insulation are "oversized" and the devices are engineered for minimal failure incidents. Therefore, such devices are very bulky, limited in their functionality and require very invasive implantation procedures.

To enable new neurotechnology devices to interface effectively with the nerve system and to open up new applications, miniaturized and more flexible device structures with improved spatial and temporal sensitivity and packaging are needed. For many important applications such as the retinal implant where the shape of the implant structure needs to adapt to the curved shape of the inner eye, the substrate should be flexible to conform to the natural soft-tissue structure. That is, many types of implantable devices should ideally be biocompatible not only in the sense of chemical and biological inertness, but also in the sense of "mechanical" or "structural" biocompatibility, i.e., sufficient physical conformability and flexibility so as not to interact with surrounding tissue in an unwanted manner.

In recent years, researchers have focused on the use of flexible substrates like polyimides (or more recently liquid crystal polymers, or LCP) with hybrid assemblies of electronic chips, conduction layers and microelectrode arrays for stimulating and recording, all integrated on the flex substrate. A small footprint, high functionality, high reliability and biocompatibility are desirable attributes for active medical implants. The smaller the device, the less invasive is the procedure of implantation and one can expect better compatibility with surrounding tissue. At the same time, as noted above devices need to be packaged to have a biocompatible tissue interface and to withstand biodegradation in the body. The term biocompatibility in this context refers to mechanical biocompatibility as well as immunological biocompatibility.

The development of flexible polymer carriers for mounting and interconnecting chips and miniaturized components offer the possibility to develop micro-electronic and micro-optical systems that are in direct contact with delicate soft tissues and biological structures. Instead of standard housed IC components, bare or "naked" silicon chips and dies are used for hybrid integration to minimize component dimensions.

Unresolved critical issues in all implantable biomedical applications—and particularly for implanted neural prostheses and other devices envisioned to include flexible polymeric substrates—include packaging, integration and electrical connection of silicon dies or surface mounted electronics with the substrate and electrode arrays. Major challenges include bonding of chips or dies to flexible substrates and packaging of the device including electrical interconnects, connection pads and cables/leads. Protecting the implant from the corrosive effects of the biological fluids has been a particular challenge. Insulating biomaterials intended for implants need to protect devices from the hostile body environment for the lifetime of an implant recipient, sometimes for decades. Not only does the packaging need to withstand biodegradation in the body, but also the materials need to be biocompatible to prevent adverse reactions from the surrounding tissue. To date, the goal of a functional neural implant device that can survive for years in-vivo or in vitro has not been achieved.

Several companies use flip-chip processes to produce miniaturized turnkey electronic assemblies for medical implants, micro/miniature wireless devices, and a host of other applications. In addition to solder bumps, flip-chip technology has also employed gold wire stud bumps. Additionally, Parylene coatings have been employed for passivation to assemble a prototype implantable retina prosthesis with secondary receiving power and data coils. Researchers at the University of Utah are developing flip-chip assembly techniques to surface-mount chips directly on the back of a Si probe. See Solzbacher F., *Chronic microelectrode arrays*, Contract NINDS-NIH N01-NS-4-2362 (2004-2008). As a modification of traditional flip-chip processing, a group at the Fraunhofer Institute for Biomedical Engineering, St. Ingbert, Germany has developed a flexible interconnection technology to interconnect chips and surface-mount passive devices (SMD) with ultra-thin highly flexible polyimide (PI) substrates for a retinal implant using gold balls instead of solder bumps to connect the IC and substrate. See Stieglitz et al., *Micromachined, polyimide-based devices for flexible neural interfaces*, Biomed. Microdevices. 2(4): 283-294 (2000); Meyer et al., *High density interconnects and flexible hybrid assemblies for active biomedical implants*, IEEE Trans. Adv. Pack. 24: 366-374 (2001). This new assembly process is known as MicroFlex Interconnection (MFI). First, the PI substrate with metal traces and connection pads with a central via is microfabricated. The vias are aligned with the bond pads of the IC and a gold ball is bonded through the vias in the PI onto the metal pads of the chip utilizing a common thermosonic ball-bumping process. The gold ball acts as a stud or metal "rivet" to electrically connect and mechanically fix the chip or SMD to the substrate. This is a similar bonding scheme to flip-chip with gold studs replacing solder bumps. Because bonding occurs only at the through-via sites in the PI cable, an epoxy material is filled between the ribbon cable and the IC or SMD to improve stability of the connection. See Stieglitz et al., *Micromachined, polyimide-based devices for flexible neural interfaces*, Biomed. Microdevices. 2(4): 283-294 (2000).

Known technologies such as discussed above have not adequately addressed the above-mentioned problems. For instance, even with the use of underfill material, solder bumps, metal balls, rivets, and other conventional interconnects still represent potentially weak connection points, both structurally and electrically, between the chip or die and underlying substrate. These types of interconnects as well as the underfill material may still be prone to degradation in an environmentally or biologically hostile environment. Accordingly, mechanical stability, operational or functional reliability, biocompatibility, service life, etc. are still compromised in conventional packaged electronic devices. Moreover, sufficient miniaturization as needed for advanced devices such as electrostimulation devices has not been attained. As an example in the case of an intraocular implant such as an artificial retina, it is estimated that up to 1000 electrical neurostimulation sites are needed to restore useful vision in blind people. See Margalit et al., *Retinal prosthesis for the blind*, Survey Ophth. 47: 334-356 (2002). Currently, state-of-the-art retina chips have been designed and fabricated in the standard CMOS process with 1.5-μm feature size through the MOSIS foundry (Marina Del Rey, Calif.) to address up to 64 sites on a 4.6 mm×4.6 mm chip at the University of Michigan. See Ghovanloo et al., *A modular 32-site wireless neural stimulation microsystem*, IEEE J. Sol. State Cir. 39:1-10 (2004). Other groups in the USA and in Europe have built chips with similar capabilities and size. See Liu et al., *A neuro-stimulus chip with telemetry unit for retinal prosthetic device*, IEEE J. Sol. State Cir. 35: 1487-1497 (2000). It is not clear whether current technology is sufficient to enable engineers to design and build the circuitry to stimulate 1000 sites and package the circuitry into a single chip with this footprint because of limitations in the I/O and connections to substrate and the required voltage to stimulate neurons. Most likely, through the use of current technology, several chips would need to be mounted on the flex substrate to attain the required performance and functionality.

Therefore, in view of the foregoing, despite some advances in microfabrication technologies pertaining to packaged electronic devices, it is well-recognized by persons skilled in the art that an ongoing need exists for providing improved packaged electronic devices and related methods, apparatus and systems.

SUMMARY

According to one implementation, a packaged electronic device is provided. The packaged electronic device includes a die, a flexible circuit structure bonded directly to the die, and a barrier film disposed on the die. The packaged electronic device includes a substrate including a first substrate surface and an opposing second substrate surface, die circuitry formed on the substrate, and a plurality of electrical contacts located on the first substrate surface and communicating with the die circuitry. The flexible circuit structure includes a first structural layer, a plurality of electrical conductors, and a second structural layer. The first structural layer is bonded directly to the first substrate surface and has a plurality of first openings respectively aligned with the plurality of electrical contacts. Each electrical conductor is disposed on the first structural layer and extends through a respective first opening into contact with a respective electrical contact. The second structural layer is disposed on the electrical conductors and has a plurality of second openings defining respective exposed areas on the electrical conductors. The electrical conductors are encapsulated by the first structural layer and the second structural layer. The electronic device is encapsulated by the barrier film and one or more of the first structural layer and the second structural layer.

According to another implementation, a method is provided for fabricating a packaged electronic device. A flexible circuit structure is fabricated on a first substrate surface of a substrate by: depositing a first structural layer on the first substrate surface wherein the first structural layer is bonded directly to the first substrate surface, forming a plurality of electrical conductors on the first structural layer and in signal communication with die circuitry of the substrate, and depositing a second structural layer on the electrical conductors, wherein the electrical conductors are embedded between the first structural layer and the second structural layer. The flexible circuit structure in combination with the substrate forms an electronic device. A barrier film is deposited on a second substrate surface of the substrate opposite to the first substrate surface, and on an outer lateral surface of the substrate extending generally between the first substrate surface and the second substrate surface, wherein the electronic device is encapsulated by the barrier film and one or more of the first structural layer and the second structural layer.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1A:
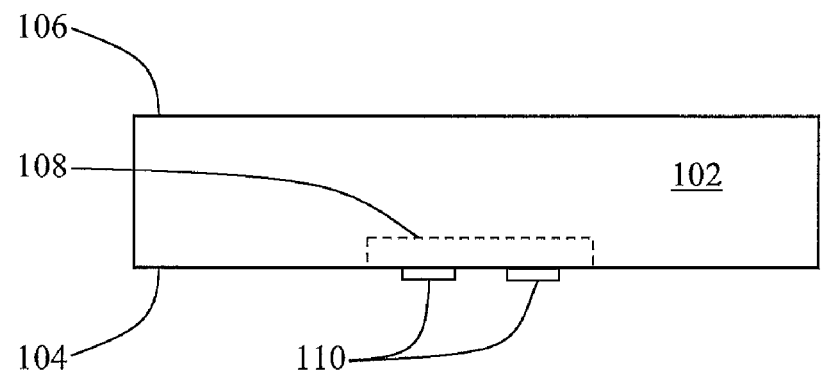
FIGS. 1A-1J are elevation views illustrating an example of a method for fabricating a packaged electronic device.

For convenience, the term "implantable" as used herein is intended to encompass not only devices that may be installed and operated within a living organism but also devices that may be attached to the outer skin of a living organism.

As used herein, the term "biocompatible," in the context of a material or device intended for in vivo implantation, generally means that the material or device after implantation will not have toxic or otherwise injurious effects at the local level (e.g., surrounding tissue) or systemic level. "Biocompatible" also means structurally or mechanically compatible, in that the material or device after implantation is able to perform its intended function or provide its intended therapeutic effects while minimizing adverse physical effects in surrounding tissue. Generally, a structurally or mechanically compatible material or device is sufficiently flexible so as to be conformable with the surrounding tissue.

In general, the term "communicate" (for example, a first component "communicates with" or "is in communication with" a second component) is utilized in the present disclosure to indicate a structural, functional, mechanical, electrical, optical, magnetic, ionic or fluidic relationship between two or more components (or elements, features, or the like). As such, the fact that one component is said to communicate with a second component is not intended to exclude the possibility that additional components may be present between, and/or operatively associated or engaged with, the first and second components.

For purposes of the present disclosure, it will be understood that when a given layer (or film, region, substrate, component, device, structure, or the like) is referred to as being "on" or "over" another layer, or "bonded to" another layer, that given layer may be directly or actually on (or over, or bonded to) the other layer or, alternatively, intervening layers (e.g., buffer layers, transition layers, interlayers, sacrificial layers, etch-stop layers, masks, electrodes, interconnects, contacts, or the like) may also be present. A given layer that is "directly on" another layer at the juncture between the two layers, or "bonded directly to" another layer, means that no intervening layer is present, unless otherwise indicated. It will also be understood that when a given layer is referred to as being "on" (or "over") another layer, or "bonded to" another layer, that given layer may cover the entire surface of the other layer or only a portion of the other layer. It will be further understood that terms such as "formed on," "disposed on," "bonded to" and the like are not intended to introduce any limitations relating to particular methods of material transport, deposition, fabrication, surface treatment, or physical, chemical, or ionic bonding or interaction, unless otherwise indicated.

As used herein, the term "die" refers to a piece or body of material on which electronic (or electrical) circuitry (i.e., die circuitry) has been fabricated. Typically in the context of integrated circuits, as appreciated by persons skilled in the art, several copies of the same integrated circuit may be fabricated on a relative large wafer or substrate of semiconducting material. The semiconducting wafer is then diced, or cut into several pieces, with each resulting piece being a die containing a respective one of the circuits. In the context of the present disclosure, however, the material comprising the die, or in the case of dicing operations the larger substrate from which the die is formed, is not limited to being a semiconducting material.

FIGS. 1A-1J illustrate an example of a method for fabricating a packaged electronic device that includes a die integrated with a flexible circuit structure in accordance with the present teachings.

Referring to FIG. 1A, a rigid substrate or wafer 102 is provided. The substrate 102 may have any suitable composition and thickness, so long as the substrate 102 is rigid enough to serve as a free-standing substrate capable of supporting the building of a flexible circuit structure as described below. Moreover, the substrate 102 must be compatible with the process steps taken to build the flexible circuit structure. For instance, in cases where the building of the flexible circuit structure entails thermal curing, the substrate 102 must be capable of withstanding such thermal curing. As other examples, again depending on the process undertaken for fabricating the flexible circuit structure, the substrate 102 may also need to be compatible with developer chemicals, etchants, etc. The substrate 102 may be electrically conductive, semiconducting, or insulating. The substrate 102 may be an elemental metalloid or semiconductor (e.g., silicon), a semiconductor compound such as a Group III-V compound (e.g., GaN and related compounds) or other semiconductor compounds and alloys (e.g., SiC, SiGe, GaAs, InGaP, etc.), a glass, ceramic, a dielectric, a polymer, or a metal. In one non-limiting example, the substrate 102 is a silicon (Si) wafer having a thickness (in the vertical direction from the perspective of FIG. 1A) of 250 µm. The substrate 102 includes a first surface 104 and an opposing second surface 106, the thickness of the substrate 102 being generally defined as extending between and including the first surface 104 and the second surface 106.

In this context, terms such as "first" and "second" are arbitrary as no limitations are placed on a particular orientation of the substrate 102 or any other component of the packaged electronic device being described. For instance, either the first surface 104 or the second surface 106 could be a bottom surface, an inside surface, a top surface, an outside surface, etc. Moreover, it will be understood that the illustrated substrate 102 may represent a portion or section of a full wafer of substrate material. Such a wafer may have a diameter of, for example, four, six or twelve inches. Accordingly, persons skilled in the art will appreciate that FIGS. 1A-1J may be representative of the use of a large wafer or substrate 102 and the simultaneous microfabrication of several dies and corresponding flexible circuit structures.

Continuing with FIG. 1A, die circuitry 108 (e.g., one or more electrical circuits or devices) is formed at (on and/or into) the first surface 104 of the substrate 102 by any suitable technique. The specific technique selected may depend on a number of factors, including the features and/or functions of the die circuitry 108. The die circuitry 108 may include active attributes (e.g., transistors, p-n junctions, active sensors, etc.) and/or passive attributes (e.g., resistors, capacitors, inductors, thermistors, conductive leads, ground planes, passive sensors, etc.). In addition, one or more electrical contacts 110 (e.g., bond pads) are formed on the die circuitry 108 by any suitable technique that results in electrical communication between the electrical contacts 110 and the die circuitry 108.

The electrical contacts 110 may be composed of, for example, a suitably conductive metal (e.g., copper (Cu), gold (Au), silver (Ag), aluminum (Al), platinum (Pt), palladium (Pd)), metal alloy (e.g., platinum-iridium (Pt—Ir)), an optically transparent compound (e.g., indium tin oxide (ITO)), graphite, a conductive polymer, etc. One example of forming the electrical contacts 110 entails depositing a metallization layer by a suitable vacuum deposition technique or electroplating followed by patterning according to known techniques. Other non-limiting examples include depositing the material by evaporation, screen-printing, spin-on coating, etc.

Figure 1B:
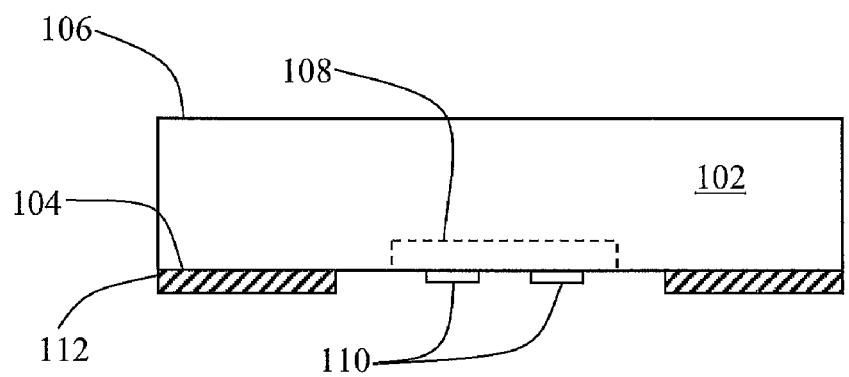

Referring to FIG. 1B, a sacrificial release film 112 is formed on the first surface 104 of the substrate 102. The release film 112 may have any composition suitable for serving as a sacrificial material. As non-limiting examples, the release film 112 may be a metal (e.g., Al, chromium (Cr), etc.), an oxide (e.g., $SiO_2$), a nitride (e.g., $Si_3N_4$), or a polymer. The release film 112 may formed by any technique suitable for its composition. As an example, in the case of a metal release film 112 such as Al or Cr, the release film 112 may be formed by sputter deposition and patterning according to known techniques. The patterning is such as to leave the electrical contacts 110 exposed as well as areas of the first surface 104 to which the flexible circuit structure is to be directly bonded. No specific limitation is placed on the thickness of the release film 112. In one specific example, the thickness of the release film 112 is 200 nm.

Figure 1C:
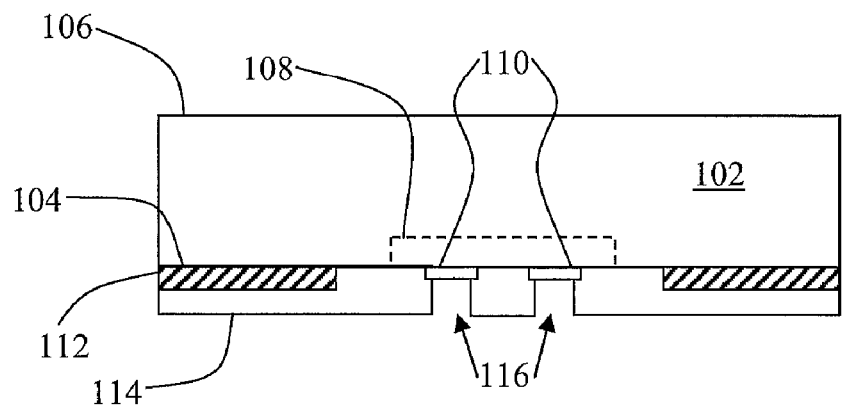

Referring to FIG. 1C, a first structural layer 114 is formed on the first surface 104 of the substrate 102 by any technique suitable for the composition of the first structural layer 114, and which results in the first structural layer 114 covering the release film 112 while defining openings or vias 116 that leave the electrical contacts 110 of the substrate 102 exposed (i.e., the openings 116 are aligned with the electrical contacts 110). The first structural layer 114 may have any suitable electrically insulative composition for this purpose. In addition, the as-deposited material of the first structural layer 114 should be flexible. A few non-limiting examples include polymers such as polyimide or polyparaxylylene (e.g., the class of Parylenes). Throughout this disclose, it will be understood that the term "polyimide" encompasses copolymers of polyimide and blends of polyimide. In advantageous implementations, the first structural layer 114 is a polymer of the type that can be deposited by a spin-on coating process although other material-additive processes such as dip coating may be suitable. In further advantageous implementations, the first structural layer 114 is a polymer that includes an adhesion promoter, one specific example being a photo-definable polyimide precursor solution such as commercially available from HD Microsystems, Parlin, N.J. and designated PI2723 or also commercially available from Fujifilm Electronic Materials U.S.A. Inc., Queen Creek, Ariz. and designated Durimide 7020. The adhesion promoter may be of the type designed to provide covalent bonds to the surface of the substrate 102. For instance, in the case where the substrate 102 is silicon, the surface of the substrate 102 to which the first structural layer 114 is bonded may be composed of $SiO_2$ (such as by thermal oxidation) or $Si_3N_4$, in which case the adhesion promoter is designed to covalently bond to such composition. Generally, the built-in adhesion promoters provided with these polyimide precursor solutions have been found to provide excellent adhesion to surfaces such as cured polyimide, $SiO_2$, $Si_3N_4$, Si, Al, Au, and Cu. In this latter example, the polyimide is spun-on, soft-baked (e.g., at 60° C.) to remove the solvents of the precursor solution, patterned by any suitable technique (e.g., UV lithography, laser ablation, lift-off, dry etching, wet etching, etc.) and then thermally cured (e.g., at 300° C.). More generally, an adhesion promoter may be selected for use in conjunction with a variety of compositions of the surface of the substrate 102, including silicon, glass, quartz, ceramics, metals, inorganic oxides, inorganic nitrides, and polyimides. The portion of the first structural layer 114 that covers the release film 112 may have any suitable thickness. In one specific example, the thickness of the first structural layer 114 is 5 μm.

As an alternative or in addition to the first structural layer 114 including a built-in adhesion promoter, an adhesive layer (not specifically shown) may be applied between the first substrate surface 104 and the first structural layer 114. For example, an adhesive coating may be applied to the first substrate surface 104 prior to depositing the material of the first structural layer 114. The adhesive coating may have any composition suitable for promoting or enhancing adhesion of the first structural layer 114 to the first substrate surface 104. Examples of an adhesive coating include, but are not limited to, a silanizing agent. Such an adhesive coating may be applied by spin-on coating, spray-on coating, dip coating, or the like.

Figure 1D:
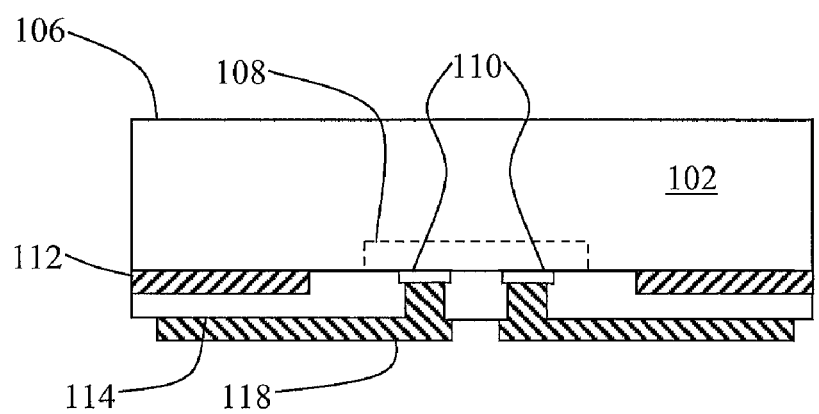

Referring to FIG. 1D, electrical conductors (e.g., traces) 118 are formed so as to extend along at least a portion of the first structural layer 114 and fill in the openings 116 (FIG. 1C) defined by the first structural layer 114 so as to communicate with the electrical contacts 110. In a typical implementation contemplated by the present teachings, the material utilized for forming the electrical conductors 118 is a metal or metal alloy. The metal or metal alloy may be deposited by any suitable technique, such as a vacuum deposition technique, for instance a physical vapor deposition (PVD) technique such as sputtering. In some implementations, two or more layers of different metals are deposited to form the electrical conductors 118. As an example, the metallization may consist of first depositing Cr followed by depositing Au, where Cr may serve primarily as an adhesion layer. The portion of the metal film that covers the first structural layer 114 may have any suitable thickness. In one specific example entailing the deposition of a bilayer of Cr and Au, the thickness of the Cr is 20 nm and the thickness of the Au is 200 nm As one non-limiting example of forming the electrical conductors 118, the deposited metal film is patterned by utilizing a photoresist etch mask (e.g., Shipley 1813, commercially available from Shipley Co. Inc., Freeport, N.Y.) and chemical wet etchants to define the electrical conductors 118.

Figure 1E:
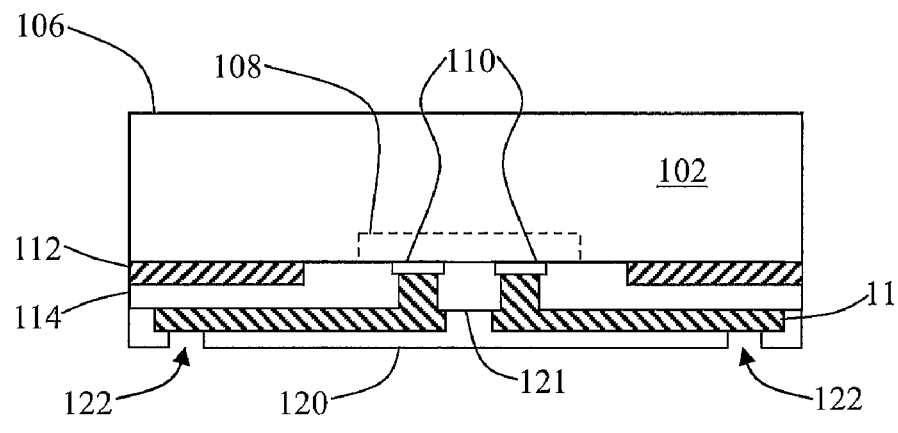

Referring to FIG. 1E, a second structural layer 120 is deposited so as to encapsulate the electrical conductors 118 while leaving openings 122 that define electrical contact areas on the electrical conductors 118. As illustrated, portions 121 of the second structural layer 120 may be deposited directly on corresponding portions of the first structural layer 114 so as to fully encapsulate and isolate edges of the electrical conductors 118. The composition of the second structural layer 120 may be the same or different from that of the first structural layer 114. The second structural layer 120 may be deposited by any technique suitable for its composition. In some implementations, the second structural layer 120 is polyimide. As in the case of the first structural layer 114, the second structural layer 120 in this example may be deposited by spin-on coating, soft-baked, patterned and then thermally cured. The second structural layer 120 may have any suitable thickness. In one specific example, the thickness of the second structural layer 120 is 5 μm. As an alternative to built-in adhesion promoters, as noted above an adhesive layer or coating may be applied to the surfaces on which the second structural layer 120 is deposited.

Figure 1F:
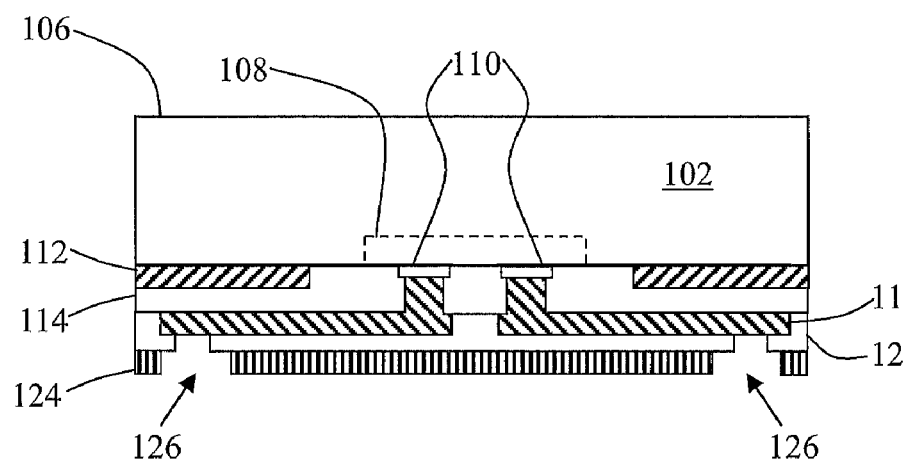

Referring to FIG. 1F, to provide enhanced protection, an additional barrier film 124 (coating, layer, etc.) may be optionally deposited onto the second structural layer 120 and patterned so as to define openings 126 in alignment with the openings 122 (FIG. 1E) defined by the second structural layer 120. The barrier coating 124 may have any suitable composition utilized in the packaging of electronics. In implementations where the packaged electronic device 170 described herein is intended for in vivo or in vitro implantation and operation, the barrier coating 124 should be biocompatible. In some implementations, the barrier coating 124 has a diamond-like carbon (DLC) inclusive composition, which may be conformally deposited by, for example, plasma-enhanced chemical vapor deposition (PECVD) utilizing a known precursor material such as, for example, an appropriate hydrocarbon. Patterning may be accomplished by, for example, a standard photoresist lift-off procedure. The barrier coating 124 may have any suitable thickness. In one specific example, the thickness of the barrier coating 124 is 300 nm. The surface properties of the DLC films utilized in this example can be engineered to yield hydrophilic or hydrophobic surface properties to improve biocompatibility, such as by adding appropriate dopants (e.g., oxygen, fluorine, etc.) or by performing a surface treatment (e.g., surface functionalization) such as plasma or wet treatment. The DLC films exhibit excellent adhesion to most plastic substrates and metals, can be easily patterned, and exhibit low moisture and oxygen permeabilities. Some examples of suitable DLC-inclusive films are described in U.S. Patent App. Pub. No. US 2002/0172938, the entirety of which is incorporated herein by reference. Other examples of the barrier coating 124 include, but are not limited to, a Parylene, amorphous $SiO_2$, and amorphous $Si_3N_4$ or combinations of the foregoing.

Depending on the specific design or purpose of the end-use article, the openings 122/126 (FIGS. 1E and 1F) to the electrical conductors 118 may be filled with an electrically conductive material to provide electrode contacts such as, for example, bond pads (not shown). As one example, the openings 122/126 may be filled with a Pt—Ir alloy by sputter-deposition.

While the illustrated example provides a single level of electrical conductors 118 sandwiched between the first structural layer 114 and second structural layer 120, it will be understood that additional metallization and insulation steps may be undertaken to build additional levels of electrical conductors 118 protected and isolated within additional structural layers. The additional structural layers may be patterned so as to provide vias in appropriate locations whereby each electrical conductor 118 provides signal communication between at least one electrical contact 110 associated with the die circuitry 108 and one electrode site (which may be placed in signal communication with another device external to or remote from the die circuitry 108).

Figure 1G:
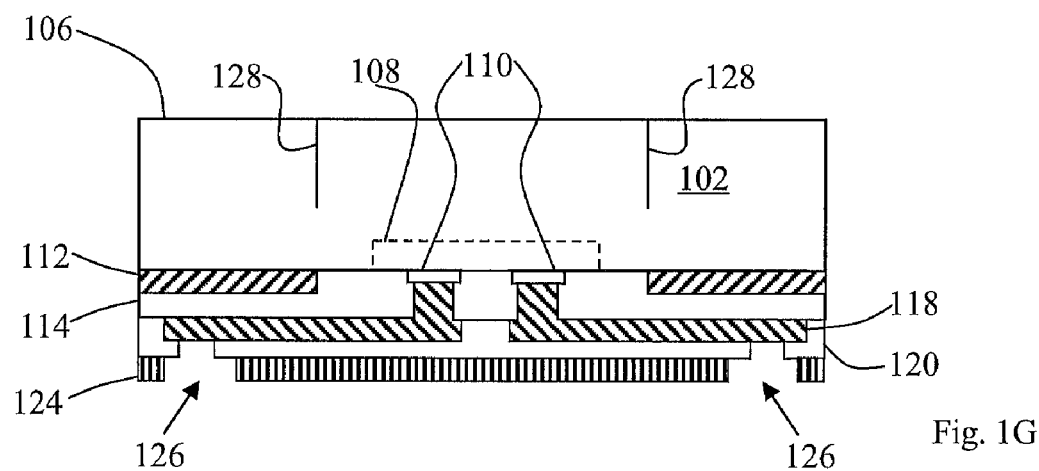

Referring to FIG. 1G, the substrate 102 is partially diced into individual dies as indicated by partial cut lines 128 depending into the thickness of the substrate 102 from its second surface 106. The partial dicing may be accomplished by any suitable means such as, for example, a wafer saw.

Figure 1H:
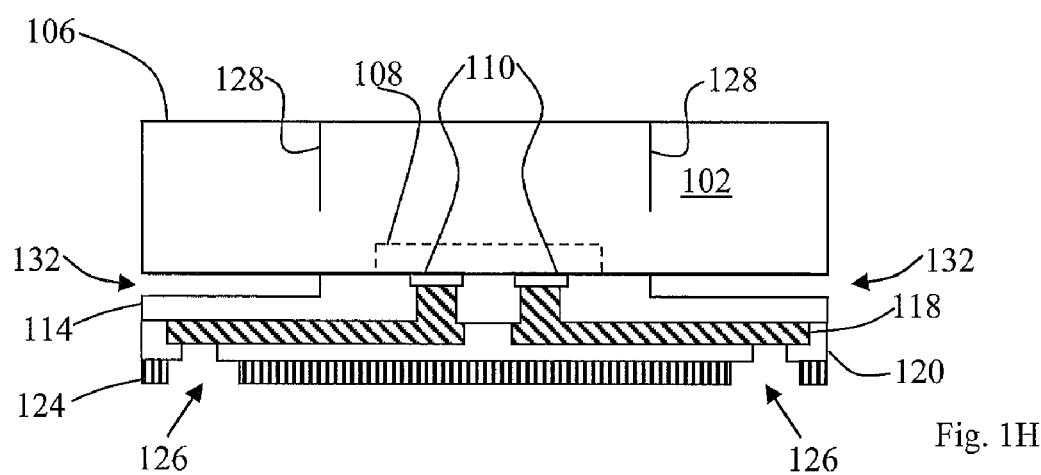

Referring to FIG. 1H, the sacrificial release film 112 (FIGS. 1B-1G) is removed by any means suitable for the composition of the release film 112, thereby creating gaps 132 generally between the portions of the substrate 102 to be removed and the flexible circuit structure being built. As one non-limiting example where the release film is Cr, a chromium etchant may be utilized such as is commercially available from Cyantek Corporation, Fremont, Calif.

Figure 1I:
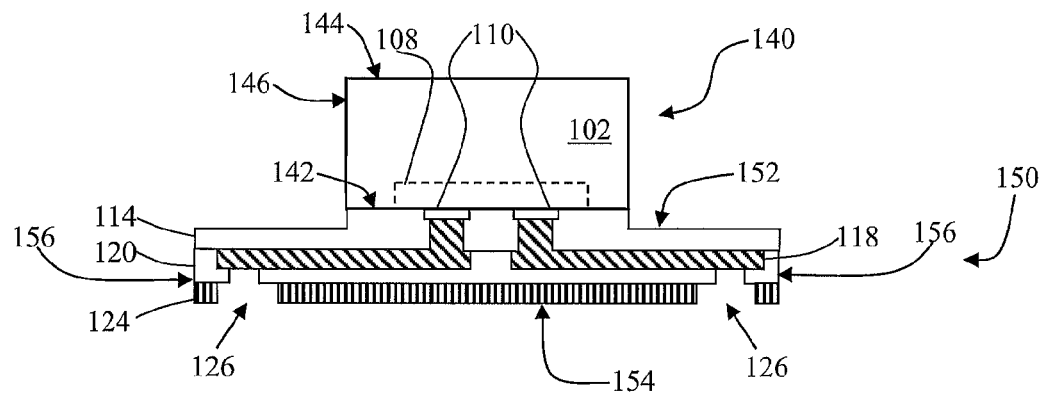

Referring to FIG. 1I, the substrate 102 is then broken along the partial cuts 128 (FIG. 1H), thereby leaving individual dies 140 bonded to (and integrally formed with) resulting flexible circuit structures 150. It will be understood that while FIG. 1I illustrates a single die 140 bonded to a single flexible circuit structure 150, several dies 140 and corresponding flexible circuit structures 150 may be fabricated simultaneously as appreciated by persons skilled in the art. In advantageous implementations where the first structural layer 114 is a polyimide or other polymer that is formulated with an adhesion promoter, or an adhesive layer or coating is provided as described above, the resulting die 140 is chemically bonded to the flexible circuit structure 150. Each die 140 includes an inner side 142 generally facing and bonded to the flexible circuit structure 150, an opposing outer surface 144, and outer lateral surfaces 146 generally extending between the inner side 142 and the outer surface 144. Each flexible circuit structure 150 includes an inner side 152 generally facing and bonded to the die 140, an opposing outer side 154 in which the openings 126 to the electrical conductors 118 are provided, and opposing lateral sides 156 extending along the thickness of the flexible circuit structure 150 between the inner side 152 and the outer side 154. It can be seen that with the exception of the openings 126 left for providing external electrical connection to the flexible circuit structure 150, all electrically conductive components of the flexible circuit structure 150 are completely encapsulated by the first structural layer 114 and the second structural layer 120. Moreover, the electrical contacts 110 that provide the interconnection between the die circuitry 108 and the flexible circuit structure 150 are completely embedded within or between the die 140 and the flexible circuit structure 150.

Figure 1J:
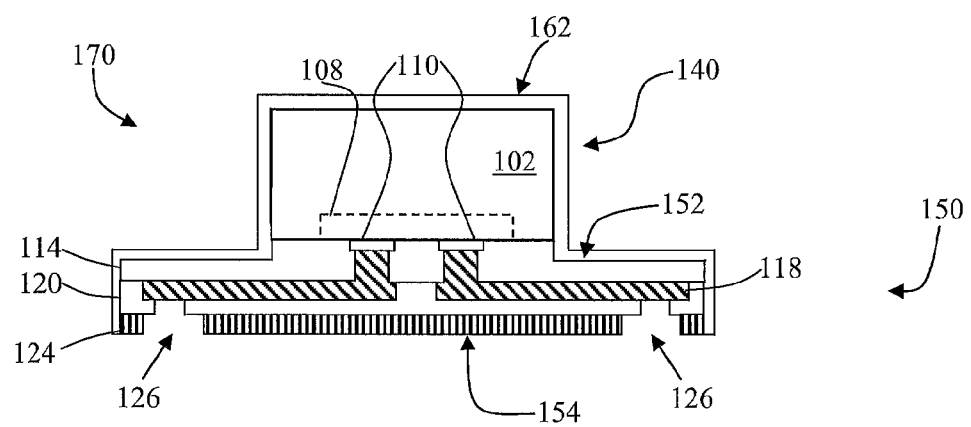

Referring to FIG. 1J, packaging may be completed by forming a conformal protective barrier film 162 that covers, at least, all remaining exposed surfaces of the article, including the outer surface 144 and lateral surfaces 146 of the die 140. The composition of the barrier film 162 may be the same as or different from the compositions of the first structural layer 114 and the second structural layer 120. As one non-limiting example, the barrier film 162 may include a polyimide layer. Because the three-dimensional topography of the as-built device does not facilitate the application of initially liquid coatings via conventional spin-coating, a modified spray-spin-coating process may be performed to apply the polyimide coating. As an example, the liquid dispenser conventionally utilized for spin-coating may be replaced by a spray nozzle (such as a FullJet® spray nozzle commercially available from Spraying Systems Co., Wheaton, Ill.), which provides a full cone spray pattern (e.g., four-inch diameter) of the polyimide precursor solution while the substrate 102 is rotated in a conventional spin coater. Alternatively, the barrier film 162 may be a composite barrier structure that includes an additional protective layer (such as, for example, the above-described DLC-inclusive coating) on the polyimide (or other polymer) layer as described above. In one specific example, the barrier film 162 is formed by depositing a polyimide layer in a spray coating process, which is optionally followed by deposition of a DLC-inclusive coating or other additional protective coating. As illustrated by example in FIG. 1J, the barrier film 162 may additionally cover exposed portions of the inner side 152 of the flexible circuit structure as well as the lateral sides 156 of the flexible circuit structure, although these areas may already be adequately protected by the existing first structural layer 114, second structural layer 120, and optional barrier coating 124.

The resulting article illustrated in FIG. 1J is a fully encapsulated electronic device 170. The total thickness of the completed flexible circuit structure 150 may range from 5 μm to 50 μm. In another example, the total thickness of the completed flexible circuit structure 150 may range from 10 to 25 μm. The total thickness of the encapsulated electronic device 170 may range from 10 μm to 400 μm. In another example, the total thickness of the encapsulated electronic device 170 may range from 50 μm to 250 μm.

In implementations where the outermost surfaces of the electronic device 170 (e.g., the barrier film 162 and the second structural layer 120, or the barrier film 162 and the barrier coating 124 applied to the second structural layer 120) are composed of biocompatible materials, the resulting electronic device 170 is suitable for in vivo or in vitro implantation and operation. Moreover, it can be seen that the die 140 and the flexible circuit structure 150 are bonded directly to each other and thus fully integrated with each other as a unitary electronic device 170. There is no separation of the die 140 and the flexible circuit structure 150 by solder bumps, layers of underfill materials, or other features conventionally required for spacers, electrical interconnects, structural rigidity, and the like. As a consequence, intimate contact is formed between the die 140 and the flexible circuit structure 150 with improved seals for all points of electrical contact, improved biocompatibility, and increased mechanical stability of the areas of contact between the die 140 and the flexible circuit structure 150. Hence, by microfabricating the flexible circuit structure 150 directly on the rigid substrate 102 and bonding the material of the first structural 114 to a large surface area of the die 140, many of the potentially weak connection points in this type of device are eliminated and the electrical components of the die 140 and the flexible circuit structure 150 are intrinsically encapsulated by the microfabrication process.

FIGS. 2A-2D illustrate an example of a method for fabricating a through-wafer interconnect (TWI) structure. According to implementations of the present disclosure, the TWI structure may be utilized as a substrate 202 that supports the microfabrication of a flexible circuit structure such as described above. The TWI structure may serve as an interposer wafer that electrically interconnects active and/or passive circuitry to the flexible circuit structure.

Figure 2A:
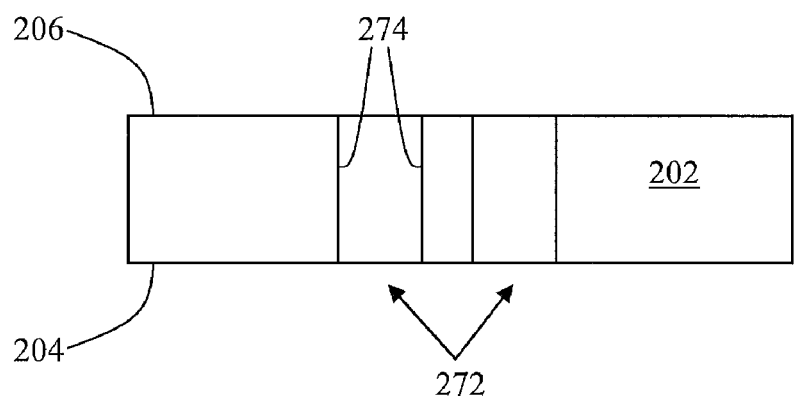
FIGS. 2A-2D are elevation views illustrating an example of a method for fabricating a substrate having through-wafer interconnects.

Referring to FIG. 2A, a substrate 202 is provided. The substrate 202 may be a silicon wafer or have any other suitable composition, and may have any thickness suitable for supporting the building of a flexible substrate structure, as described above. In one representative example, the substrate 202 has a thickness of 250 μm. As a preparatory step, the substrate 202 may be double-side polished by any suitable technique such as CMP, etching, or the like. The substrate 202 includes a first surface 204 and an opposing second surface 206, the thickness of the substrate 202 being generally defined as extending between and including the first surface 204 and the second surface 206. As before, it will be understood that the illustrated substrate 202 may represent a portion or section of a full wafer of substrate material.

Continuing with FIG. 2A, a plurality of through-holes or vias 272 with vertical side walls 274 is formed through the entire thickness of the substrate 202. For simplicity, only two such vias 272 are shown with the understanding that an array of a relatively large number of vias 272 may be formed. The vias 272 may be formed by any means suitable for the composition of the substrate 202 and utilized in precision microfabrication, such as for example mechanical drilling (typically with the use of a diamond drill bit), laser drilling, ultrasonic milling, or dry etching. In the case of a silicon wafer or the like, deep reactive ion etching or DRIE (e.g., the Bosch process) may be utilized. The diameter of the vias 272 may range from 4 μm to 100 μm. In another example, the diameter of the vias 272 ranges from 10 μm to 75 μm. In one specific example, the diameter of the vias 272 is 50 μm. The pitch of (or spacing between) the vias 272 may range from 10 μm to 1000 μm. In another example, the pitch of the vias 272 ranges from 50 μm to 500 μm. In one specific example, the pitch of the vias 272 is 150 μm.

Figure 2B:
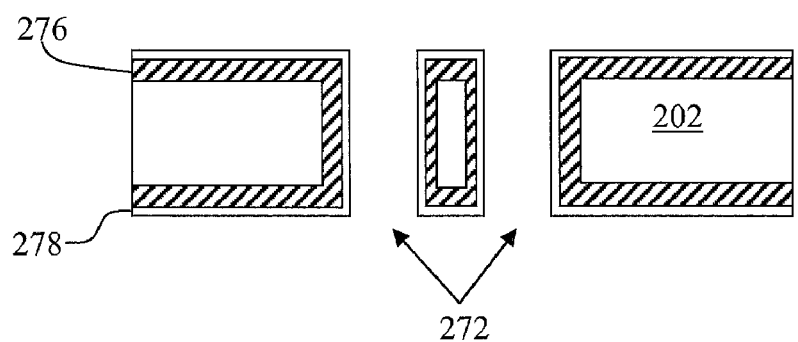

Referring to FIG. 2B, a conformal layer of insulation 276 is deposited on all exposed surfaces of the substrate 202, including the walls 274 (FIG. 2A) of the vias 272, to passivate the surfaces of the substrate 202 and electrically insulate the substrate 202 from subsequently fabricated electrically conductive components and features. Any suitable insulative material that can be applied by conformal deposition may be utilized, a few examples being oxides such as $SiO_2$, nitrides such as $Si_3N_4$, and the class of Parylenes. Any deposition method suitable for the composition of the insulating layer 276 may be employed. A typical example is a vacuum deposition technique such as chemical vapor deposition (CVD). After depositing the insulating layer 276, a conformal metal seed layer 278 is typically deposited. Any metal that facilitates the subsequent filling of the vias 272 with interconnect material may be utilized, one non-limiting example being Cu. The metal seed layer 278 may include an adhesion layer such as, for example, Cr, the deposition of which is followed by deposition of the Cu or other metal. Any suitable technique for depositing the material(s) comprising the seed layer 278 may be employed, one non-limiting example being physical vapor deposition or PVD (e.g., sputtering).

Figure 2C:
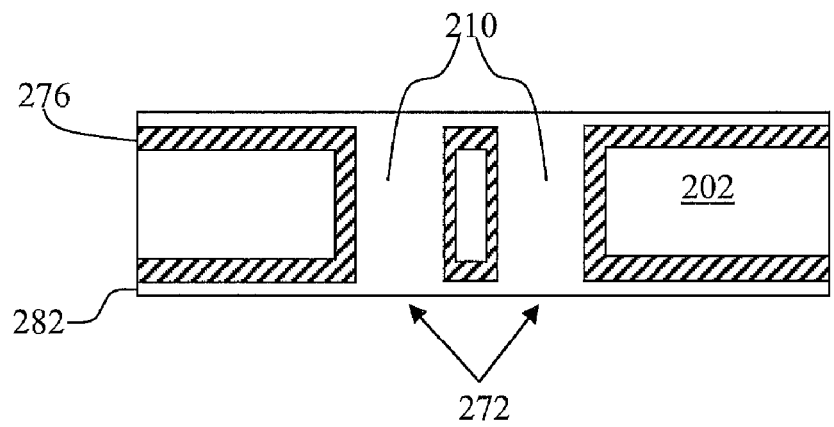

Referring to FIG. 2C, a bulk material 282 utilized for forming electrically conductive interconnects 210 is then deposited. Typically, the bulk material 282 is a metal such as Cu. Typically, the bulk material 282 is deposited on the insulating layer 276 at the first surface 204 and second surface 206 (FIG. 2A) of the substrate 202, and fills the vias 272, by electroplating. During the electroplating process, the bulk material 282 merges with the metal seed layer 278 (FIG. 2B) to form the interconnects 210, which may be solid as in the illustrated example or alternatively may be hollow.

Figure 2D:
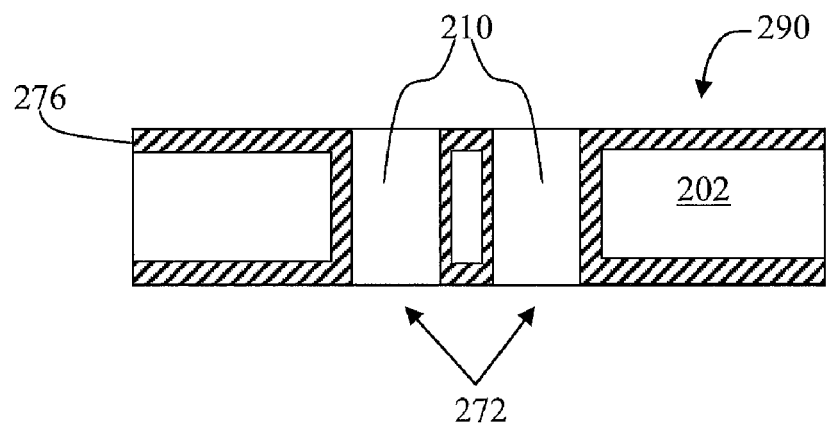

Referring to FIG. 2D, both the first surface 204 and the second surface 206 (FIG. 2A) of the substrate 202 are then planarized to remove all excess metallization. As one example, planarization may be accomplished by means of chemical-mechanical polishing (CMP), etching, or the like. The resulting article is a TWI substrate 290 that may be utilized in the fabrication of encapsulated electronic devices in accordance with certain implementations taught in the present disclosure. In one example, the density of the through-wafer interconnects 210 is 4000 $TWI/cm^2$ or greater, although less density may be provided if desired.

FIGS. 3A-3D illustrate another example of a method for fabricating a packaged electronic device that includes a die integrated with a flexible circuit structure in accordance with the present teachings. In this example, a TWI substrate or wafer 302, which may for example be prepared and fabricated such as described above and illustrated in FIGS. 2A-2D, serves as the rigid substrate 302 upon which a flexible circuit structure is fabricated.

Figure 3A:
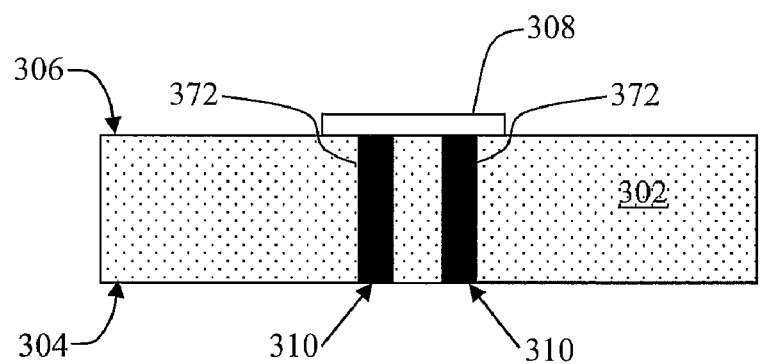
FIGS. 3A-3D are elevation views illustrating another example of a method for fabricating a packaged electronic device.

Referring to FIG. 3A, the substrate 302 includes a first surface 304 and an opposing second surface 306, and vias 372 (two being shown by example) formed through the thickness between the first surface 304 and the second surface 306 as described above. Metal interconnects 310 are disposed in corresponding vias 372. Each interconnect 310 has opposing ends in registry with the first surface 304 and the second surface 306, respectively, which may serve as first and second electrical contacts. Die circuitry 308 is formed at (on and/or into) the second surface 306 of the substrate 302 by any suitable technique whereby the die circuitry 308 electrically communicates with the ends of the interconnects 310 located at the second surface 306. The die circuitry 308 may include active and/or passive components as described above. The interconnects 310 thus provide electrical communication from the die circuitry 308, through the thickness of the substrate 302 and to the opposing ends of the interconnects 310 located at the first surface 304. The second surface 306 and the as-built die circuitry 308 may be protected by a photoresist coating (not shown) during the processing steps subsequently undertaken at the opposing first surface 304, which photoresist coating may subsequently be removed.

Figure 3B:
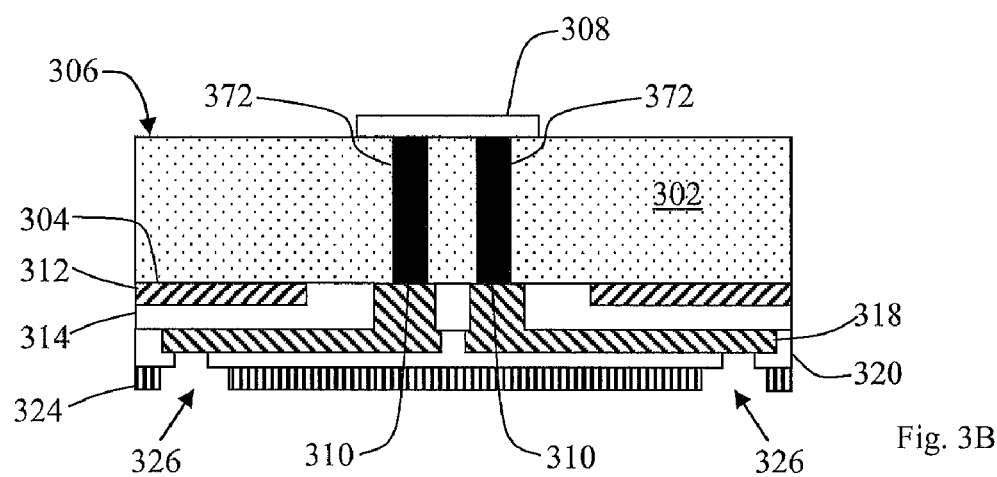

Referring to FIG. 3B, a flexible circuit structure is fabricated directly on the first surface 304 of the substrate 302. The steps taken for fabricating the flexible circuit structure may be similar to those described above in conjunction with FIGS. 1A-1J. Accordingly, a sacrificial release film 312 is formed on the first surface 304 and patterned so as to leave an area of the first surface 304 exposed for direct bonding of material of the flexible circuit structure and to leave the electrical contacts (ends of the interconnects 310) exposed. A first structural layer 314 is deposited on the first surface 304 of the substrate 302 and covers at least a portion of the release film 312, while defining openings or vias that leave the electrical contacts 310 exposed. Next, metallization or another suitable technique is performed so as to form electrical conductors (e.g., traces) 318 that extend along at least a portion of the first structural layer 314 and fill in the openings defined by the first structural layer 314. A second structural layer 320 is then deposited so as to encapsulate the electrical conductors 318 while leaving openings that define electrical contact areas on the electrical conductors 318. Optionally as described above, an additional barrier film 324 may be deposited onto the second structural layer 320 and patterned so as to define openings 326 in alignment with the openings defined by the second structural layer 320. The barrier coating 324 may be biocompatible in implementations where the packaged electronic device being fabricated is intended for in vivo or in vitro implantation and operation. It will be noted that in implementations either providing or not providing the barrier coating 324, the first structural layer 314 and the second structural layer 320 may likewise be biocompatible. As also described above, depending on the specific design or purpose of the end-use article, the openings 326 to the electrical conductors may be filled with an electrically conductive material to provide electrode sites such as, for example, bond pads (not shown).

Figure 3C:
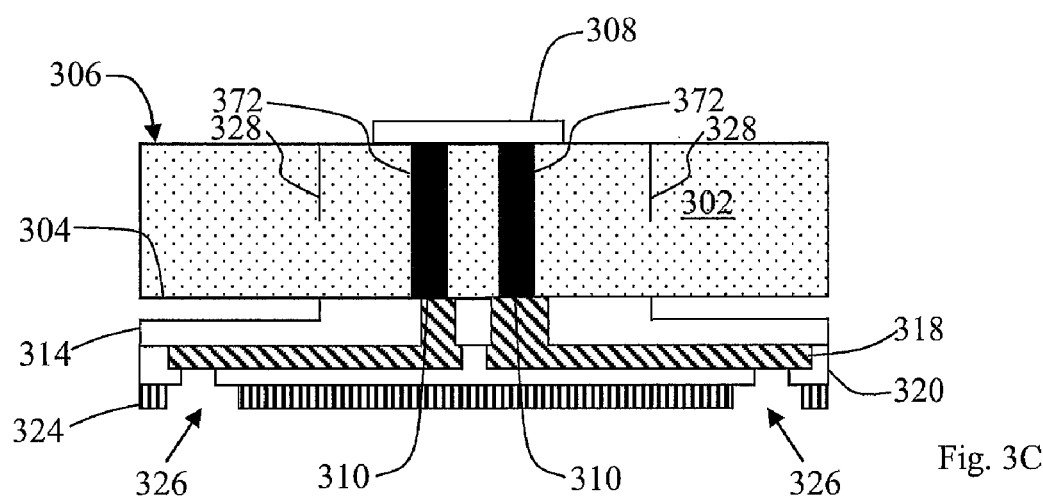

Referring to FIG. 3C, the substrate 302 is partially diced into individual dies as indicated by partial cut lines 328 depending into the thickness of the substrate 302 from its second surface 306. The sacrificial release film 312 (FIG. 3B) is removed, such as in the manner described previously.

Figure 3D:
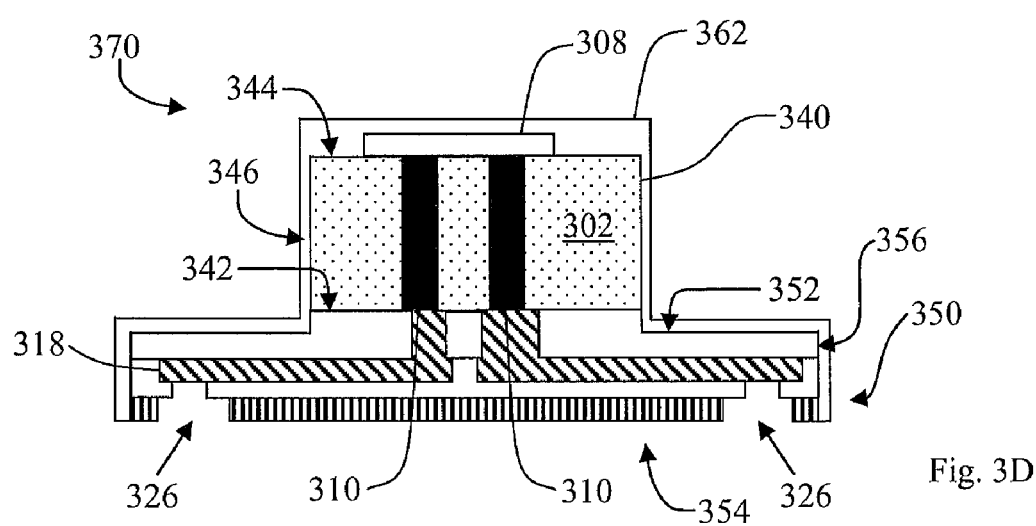

Referring to FIG. 3D, the substrate 302 is then broken along the partial cuts 328 (FIG. 3C), thereby leaving individual dies 340 bonded to (and integrally formed with) flexible circuit structures 350. In advantageous implementations where the first structural layer 314 is a polyimide or other polymer that is formulated with an adhesion promoter, the substrate 302 is chemically bonded to the flexible circuit structure 350. Adhesive layers or coatings may alternatively or additionally be utilized as described previously. Each die 340 includes an inner side 342 generally facing and bonded to the flexible circuit structure 350, as opposing outer surface 344, and outer lateral surfaces 346 generally extending between the inner side 352 and the outer side 344. Each flexible circuit structure 350 includes an inner side 352 generally facing and bonded to the die 340, an opposing outer side 354 at which the openings 326 to the electrical conductors 318 are provided, and opposing lateral sides 356 extending along the thickness of the flexible circuit structure 350 between the inner side 352 and the outer side 354. As in other implementations described above, it can be seen that with the exception of the openings 326 left for providing external electrical connection to the flexible circuit structure 350, all electrically conductive components of the flexible circuit structure 350, including the features providing the interconnection between the die 340 and the flexible circuit structure 350, are completely encapsulated by the first structural layer 314 and the second structural layer 320 (i.e., embedded within or between the die 340 and the flexible circuit 350).

The packaging for the resulting electronic device 370 may be completed by depositing a conformal protective barrier film 362 that covers, at least, all remaining exposed surfaces, including the outer surface 344 of the die 340 and the lateral surfaces 346 extending between the outer surface 344 and the inner side 342 facing the flexible circuit structure 350, as well as the die circuitry 308 present on the outer surface 344. As described above, the composition of the barrier film 362 may, for example, be a suitable polymer such as polyimide layer, or may be a composite barrier structure that includes a DLC-inclusive coating or other protective coating on the polyimide (or other polymer) layer. As illustrated by example in FIG. 3D, the barrier film 362 may additionally cover exposed portions of the inner side 352 of the flexible circuit structure 350 as well as the lateral sides 356 of the flexible circuit structure 350. The resulting article is a fully encapsulated electronic device 370.

The electronic device 370 illustrated in FIG. 3D provides all of the advantages of the electronic device 170 illustrated in FIG. 1J. In addition, the electronic device 370 enables the advantages of three-dimensional (3D) integration or "chip stacking," and represents an improved method for vertically aligning and bonding flexible circuit structures 350 to one or more dies 340. The semiconductor industry is moving to 3D integration technologies to achieve higher performance (faster signal processing, lower power consumption), smaller device size and much higher I/O count, all of which may be facilitated through the use of through-wafer interconnects. Conventionally, microelectronics are fabricated in a traditional 2D surface-mount or flip-chip approach. Device size is dictated by the number and physical dimensions of the IC chips used, and is also impacted by the discrete passive surface mount components provided. However, by stacking and interconnecting the various dies, one can expect to get a dramatic decrease in the size (footprint area) and weight of the electronics, an important consideration for implantable neural prostheses and other electronic devices contemplated by the present teachings. Vertical interconnects allow the opportunity to bond an active device to a passive component layer containing resistors, capacitors, inductances or power ground planes with a high density of interconnects. The possibility of integrating passive components such as capacitors onto the stacked device and moving them off the flex substrate will reduce device size further and eliminate reliability concern with these surface mounted devices. By stacking and vertically integrating bare dies and passive components, current processing power can be maintained or increased while maintaining or decreasing current size and weight of existing devices.

Another benefit of the approach described above in conjunction with FIGS. 3A-3D is that it has potential to be low-cost and may employ good die methods that are known to dramatically improve process yields. It is very expensive to build a flex circuit directly on an integrated circuit wafer. For cost and performance reasons, it would be very beneficial to use state-of-the-art foundries when procuring the ICs. However, fabricating a custom wafer-level IC would be very cost prohibitive and it is very wasteful to place the IC only in a small portion of the wafer. These problems can be alleviated by building the flex circuitry on a passive wafer, and then employing known good die techniques to attach a die to the backside of an interposer chip containing vertical interconnect features. This approach will ultimately lead to enhanced functionality while maintaining an extremely small form factor (size). It is also possible to separate layers or dies that handle special functions, for example one level might contain digital circuits which scale with the feature size of semiconductor processing, while another level could provide analog circuits where die real estate cannot be reduced nearly as much by going to feature sizes below 1 μm in the fabrication process.

Figure 4:
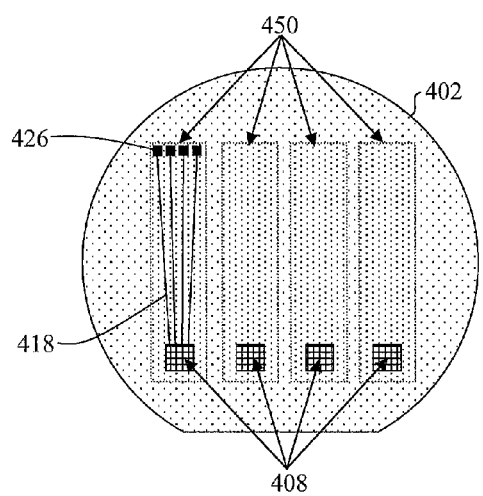
FIG. 4 is a plan view of a substrate in which a plurality of packaged electronic devices are being fabricated.

FIG. 4 is a planar view of a silicon wafer 402 as an example of a substrate on which a plurality of flexible circuit structures 450 may be fabricated. The respective footprints of the flexible circuit structures 450 are indicated by dotted lines. Four flexible circuit structures 450 are illustrated by example. The number of flexible circuit structures 450 that may be built on the surface of the wafer 402 may be more or less than four, depending on the size of the wafer 402 and the size of the flexible circuit structures 450. Die areas 408 depicted in FIG. 4 represent the footprint of the die circuitries and accompanying electrical contacts, terminations of vertical interconnects, or the like as described above in conjunction with the implementations illustrated in FIGS. 1A-3D. A plurality of electrical conductors or traces 418 are embedded within the insulating structural material utilized in building the flexible circuit structures 450 as described above, and are sufficiently isolated from each other so as to avoid cross-talk. The electrical conductors 418 provide signal communication between the electrical contacts of the die areas 408 and corresponding electrode sites or bond pads 426 formed remotely from the die areas 408. Depending on the design and purpose of the electronic devices being fabricated, the electrode sites or bond pads 426 may be physically connected or wirelessly interfaced with other electronic devices. As but one non-limiting example, the electrode sites or bond pads 426 may communicate with an electrode array utilized for in vivo/in vitro neurostimulation. FIG. 4 also illustrates that the lengths of the flexible circuit structures 450 generally in the direction of the electrical conductors 418 may be large relative to their widths. Accordingly, the flexible circuit structures 450 may serve as flexible ribbon cables in various implementations.

Figure 5:
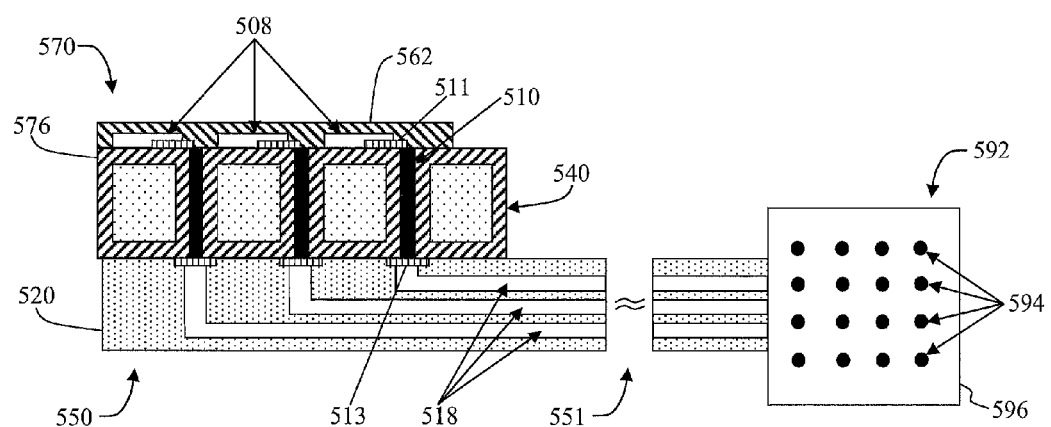
FIG. 5 is an elevation view of an example of a packaged electronic device operatively communicating with another electronic device.

FIG. 5 is an elevation view of an example of a packaged electronic device 570 fabricated in accordance with any of the implementations taught in the present disclosure. The electronic device 570 includes a die 540 integrally bonded to a flexible circuit structure 550. The die 540 may include one or more active and/or passive circuitry devices (die circuitries) 508 in signal communication with electrical contacts provided on or in the die 540. In the illustrated example, the die 540 has a TWI structure whereby interconnects 510 provide signal communication between the circuitry devices 508 formed on one side of the die 540 and embedded electrical conductors 518 of the flexible circuit structure 550 directly bonded to the opposing side of the die 540. Alternatively, the die 540 may be configured similarly to the implementation described above in conjunction with FIGS. 1A-1J, in which the circuitry devices 508 are embedded between the die 540 and the flexible circuit structure 550 and electrical communication is accomplished through embedded electrical contacts. The top side of the die 540 is encapsulated by a barrier film 562 as described above. The lateral sides of the die 540 may likewise be encapsulated by the barrier film 562 or some other insulative coating 576. For instance, in the case of utilizing a TWI structure, the insulative coating 576 may be formed during the fabrication of the TWI structure. The bottom side of the die 540 and all electrical conductors 518 of the flexible circuit structure 550 are embedded within one or more layers of structural material 520 as described above.

As further shown in FIG. 5, in some implementations electrical contacts or bond pads 511 may be formed at the top of the die 140 so as to provide signal communication between the circuitry 508 and the interconnects 510. Likewise, electrical contacts or bond pads 513 may be formed at the bottom of the die 140 so as to provide signal communication between the interconnects 510 and the respective electrical conductors 518. These electrical contacts 511 and 513 may lessen the need for precisely aligning the interconnects 510 with the circuitry 508 and the electrical conductors 518.

As further shown in FIG. 5, in some implementations some or all of the electrical conductors 518 may be arranged vertically, each level of electrical conductor(s) 518 being sandwiched between adjacent layers of structural material 520 and consequently spaced and electrically isolated from the other electrical conductors 518.

As further shown in FIG. 5, in some implementations the flexible circuit structure 550 may be appreciably long in one dimension so as to define a flexible cable portion 551 capable of carrying signals from the circuitry devices 508 to a remotely situated device 592. The remote device 592 could be any device that would benefit from cooperation with the packaged electronic device 570.

In the example illustrated in FIG. 5, the remote device 592 is an electro-stimulation device that includes an array of microelectrodes 594 supported by a substrate 596. The electro-stimulation device may be configured for neurostimulation (one example being a retinal or cranial prosthesis), muscular stimulation, or the like. Other examples of remote devices 592 include, but are not limited to, various sensors or detectors (including sensors or detectors that acquire measurements of a desired property such as electrical signals, temperature, pressure, etc., or provide an indication of a certain condition such as gas detection, biosensors, chemical sensors, etc.), optical devices, image capturing devices, radio-frequency (RF) communication devices, electro-mechanical devices, micro-electro-mechanical systems (MEMS), labs-on-a-chip, etc. The packaged electronic device 570 in combination with the remote device 592 may comprise a biocompatible electronic assembly (or device, apparatus, system, etc.) suitable for in vivo implantation. The flexibility of the cable portion 551 likewise provides significant flexibility in the design, function and operation of such an implantable electronic assembly. For instance, in the case of a retinal prosthesis, both the packaged electronic device 570 and the remote device 592 may be implanted within the eye. Alternatively, the remote device 592 may be situated outside the eye while nevertheless remaining tethered to the packaged electronic device 570 via the cable portion 551 of the flexible circuit structure 550, which may extend through the outer tissue of the eye by means of a surgical incision. Likewise, in the case of a brain signal recording device, both the packed electronic device 570 and the remote sensor 592 may be implanted in the brain. Alternatively, the remote sensor 592 may be implanted and the electronic device 570 remains outside the brain fixed to the skull but tethered to the sensor via a cable portion 551 of the flexible circuit structure 550.

The packaged electronic devices fabricated according to the implementations described herein are expected to perform well during in vitro testing, protect the underlying conductors and microelectrodes in isotonic saline solutions for several years and at the same time exhibit good biocompatibility. Accordingly, as noted throughout the present disclosure, the electronic devices taught herein are useful not only in more general or conventional applications but also in applications entailing environmental isolation or in vivo implantation.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A method for fabricating a packaged electronic device, the method comprising:
fabricating a flexible circuit structure on a first substrate surface of a substrate by:
depositing a first structural layer on the first substrate surface wherein the first structural layer is bonded directly to the first substrate surface;
forming a plurality of electrical conductors on the first structural layer and in signal communication with die circuitry of the substrate; and
depositing a second structural layer on the electrical conductors,
wherein the electrical conductors are encapsulated by the first structural layer and the second structural layer, and the flexible circuit structure in combination with the substrate forms an electronic device; and
depositing a barrier film on a second substrate surface of the substrate opposite to the first substrate surface, and on an outer lateral surface of the substrate extending generally between the first substrate surface and the second substrate surface, wherein the electronic device is encapsulated by the barrier film and one or more of the first structural layer and the second structural layer.

2. The method of claim 1, wherein the die circuitry is formed at the first surface, and fabricating the flexible circuit structure embeds the die circuitry between the flexible circuit structure and the substrate.

3. The method of claim 2, wherein the substrate includes a plurality of electrical contacts disposed at the first substrate surface in signal communication with the die circuitry, forming the plurality of electrical conductors places the electrical conductors in signal communication with the respective electrical contacts, and fabricating the flexible circuit structure embeds the electrical contacts between the flexible circuit structure and the substrate.

4. The method of claim 1, wherein the die circuitry is formed at the second substrate surface, depositing the barrier film embeds the die circuitry between the barrier film and the second substrate surface, the substrate includes a plurality of electrical interconnects in signal communication with the die circuitry and extending through the thickness of the substrate from the first substrate surface to the second substrate surface such that the electrical interconnects define respective electrical contact sites at the second substrate surface, forming the plurality of electrical conductors places the electrical conductors in signal communication with the respective electrical contact sites, and fabricating the flexible circuit structure embeds the electrical contact sites between the flexible circuit structure and the substrate.

5. The method of claim 1, wherein fabricating the flexible circuit structure includes chemically bonding the flexible circuit structure to the substrate.

6. The method of claim 1, wherein depositing the first structural layer includes chemically bonding the first structural layer to the first substrate surface.

7. The method of claim 1, wherein the composition of the first substrate surface includes a material selected from the group consisting of silicon, glass, quartz, ceramic, metals, inorganic oxides, inorganic nitrides, and polyimides, and the composition of the first structural layer includes a polymer and an adhesion promoter configured to promote chemical bonding to the composition of the first surface.

8. The method of claim 1, wherein the composition of the first substrate surface includes a material selected from the group consisting of silicon, glass, quartz, ceramic, metals, inorganic oxides, inorganic nitrides, and polyimides, the composition of the first structural layer includes a polymer, and further comprising applying an adhesive coating to at least one of the first substrate surface and the first structural layer to promote chemical bonding of the first structural layer to the first substrate surface.

9. The method of claim 1, wherein the first structural layer includes a polymer selected from the group consisting of polyimide, copolymers of polyimide and blends of polyimide.

10. The method of claim 9, wherein depositing the first structural layer includes spin-coating the polymer.

11. The method of claim 1, wherein the second structural layer includes a polymer selected from the group consisting of polyimide, copolymers of polyimide and blends of polyimide.

12. The method of claim 11, wherein depositing the second structural layer includes spin-coating the polymer.

13. The method of claim 1, wherein depositing the barrier film comprises depositing a polymer selected from the group consisting of polyimide, copolymers of polyimide and blends of polyimide.

14. The method of claim 13, wherein the depositing the barrier film comprises spraying a polymer precursor solution through a nozzle while spinning the substrate.

15. The method of claim 13, wherein the depositing the barrier film further comprises depositing an additional film on the polymer.

16. The method of claim 15, wherein the additional film includes diamond-like carbon.

17. The method of claim 1, wherein the barrier film is a first barrier film, and further comprising depositing a second barrier film on the second structural layer, wherein the electronic device is encapsulated by the first barrier film and the second barrier film.

18. The method of claim 17, wherein depositing at least one of the first barrier film and the second barrier film includes depositing a polymer selected from the group consisting of polyimide, copolymers of polyimide and blends of polyimide.

19. The method of claim 17, wherein depositing at least one of the first barrier film and the second barrier film includes depositing a polymer selected from the group consisting of polyimide, copolymers of polyimide and blends of polyimide, followed by depositing an additional barrier film on the polymer.

20. The method of claim 19, wherein the additional film includes diamond-like carbon.

21. The method of claim 1 further comprising, prior to depositing the first structural layer, depositing a sacrificial release film on the first substrate surface wherein depositing the first structural layer also deposits the first structural layer on the sacrificial release film, and after depositing the second structural layer, removing the sacrificial release film and removing a portion of the substrate to form a die directly bonded to the flexible circuit structure, the die including the die circuitry in signal communication with the flexible circuit structure.

* * * * *